United States Patent
Wood (10) Patent No.: US 7,341,061 B2
(45) Date of Patent: Mar. 11, 2008

(54) TRACHEOSTOMY SYSTEM

(76) Inventor: Scott Douglas Wood, 7515 Marquett St., Dallas, TX (US) 75225

( * ) Notice: Subject to any disclaimer, the term of this patent is extended or adjusted under 35 U.S.C. 154(b) by 0 days.

(21) Appl. No.: 11/012,587

(22) Filed: Dec. 15, 2004

(65) Prior Publication Data

US 2006/0124134 A1 Jun. 15, 2006

(51) Int. Cl.
*A61M 16/00* (2006.01)
(52) U.S. Cl. .......................... 128/207.29; 128/207.14; 128/200.24; 128/200.26
(58) Field of Classification Search .......... 128/207.29, 128/207.14, 207.15, 207.16, 200.26, 200.24, 128/205.19, 207.17, 207.18, 912, DIG. 26; 600/120

See application file for complete search history.

(56) References Cited

U.S. PATENT DOCUMENTS

| | | | | |
|---|---|---|---|---|
| 3,688,773 A | * | 9/1972 | Weiss | 128/207.29 |
| 4,141,364 A | * | 2/1979 | Schultze | 128/207.15 |
| 4,364,391 A | * | 12/1982 | Toye | 128/207.29 |
| 4,520,810 A | * | 6/1985 | Weiss | 128/207.29 |
| 4,601,713 A | * | 7/1986 | Fuqua | 604/514 |
| 4,677,978 A | * | 7/1987 | Melker | 128/207.14 |
| 4,738,666 A | * | 4/1988 | Fuqua | 604/514 |
| 4,921,479 A | * | 5/1990 | Grayzel | 604/509 |
| 5,007,900 A | * | 4/1991 | Picha et al. | 604/106 |
| 5,176,659 A | * | 1/1993 | Mancini | 604/523 |
| 5,183,464 A | * | 2/1993 | Dubrul et al. | 606/198 |
| 5,217,005 A | * | 6/1993 | Weinstein | 128/200.26 |
| 5,573,517 A | * | 11/1996 | Bonutti et al. | 604/264 |
| 5,695,469 A | * | 12/1997 | Segal | 604/104 |
| 5,823,184 A | * | 10/1998 | Gross | 128/204.18 |
| 5,957,900 A | * | 9/1999 | Ouchi | 604/264 |
| 5,997,508 A | * | 12/1999 | Lunn et al. | 604/164.08 |
| 6,190,357 B1 | * | 2/2001 | Ferrari et al. | 604/102.01 |
| 6,338,730 B1 | * | 1/2002 | Bonutti et al. | 604/509 |
| 6,613,038 B2 | * | 9/2003 | Bonutti et al. | 604/509 |
| 6,706,017 B1 | * | 3/2004 | Dulguerov | 604/164.01 |
| 7,036,510 B2 | * | 5/2006 | Zgoda et al. | 128/207.29 |

OTHER PUBLICATIONS

Bivona product I.D. for product code 850160, Fome-Cuf Tracheostomy Tube Kit (p. 1).
Fome-Cuf Users Manual (pp. 2A, 2B and 2C).
Product I.D. for Portex Adult size/ Tracheostomy Tube Holder—Ref 520000 (pp. 3A and 3B).
Photo of Shiley Tracheostomy Tubes and holders (pp. 4A-4F).

\* cited by examiner

*Primary Examiner*—Justine R. Yu
*Assistant Examiner*—Annette Dixon
(74) *Attorney, Agent, or Firm*—Akin Gump Strauss Hauer & Feld, LLP (57) ABSTRACT

A tracheostomy system includes an outer multi-layered tube, which can be expanded or allowed to contract as necessary in order to receive various sizes of cannula tubes. A dilator is used to initially insert the outer tracheostomy tube into the tracheostoma. After the initial installation dilator is removed, various sizes of dilators having a cannula mounted about them can be inserted into the outer tracheostomy tube. The multilayered tube will then expand in response to insertion of the various sizes of dilator cannula assembly being placed. When the dilator is removed the cannula tube will remain in place to maintain the desired diameter tracheostomy tube. This provides a means in which the diameter of the tube can be changed without having to actually remove and reinsert a different tube.

14 Claims, 8 Drawing Sheets

TRACHEOSTOMY SYSTEM

CROSS-REFERENCE TO RELATED APPLICATIONS

None.

STATEMENTS REGARDING FEDERALLY SPONSORED RESEARCH OR DEVELOPMENT

None.

REFERENCE TO A MICROFICHE APPENDIX

None.

BACKGROUND OF THE INVENTION

1. Field of the Invention

This invention relates to a new tracheostomy tube and tracheostomy system for performing percutaneous tracheostomy.

2. Description of the Related Art

Percutaneous placement of a tracheostomy is a very common procedure today. It is performed by making a small mid-line incision just over the trachea. Blunt dissection is used to separate the soft tissue down to the level of the tracheal rings. A needle is then placed between adjacent tracheal rings and a guide wire is inserted through the needle, usually under bronchoscopic guidance. Multiple dilators of increasing size or diameters are used to enlarge the ostomy to a sufficient diameter to accommodate the desired-sized tracheostomy tube. Various sizes of tracheostomy tubes are available and are selected based upon multiple factors, including but not limited to the size of the patient, the patient's clinical status such as the need for positive pressure ventilation or not, the quality and quantity of secretions, as well as the need for other medical procedures.

Typically, a larger tube is initially inserted into the patient, which is followed by insertion of successively smaller tubes as the patient improves and becomes less dependent on ventilator support. This requires multiple changes of the tube as the patient's clinical status improves. Of course, if a patient's clinical status worsens, then it is necessary to again install a larger tube. But, if a patient's clinical course worsens, it is sometimes difficult to insert the larger tube. This is because the ostomy site or tracheostoma usually closes very quickly as the soft tissue heals around the smaller tracheostomy tube, making it difficult and sometimes dangerous to remove a smaller tracheostomy tube and attempt to place a larger tube in its place.

Therefore, there is a longstanding need for a tracheostomy system which does not require the removal of the entire tracheostomy tube and its replacement whenever a different sized tube must be installed in a patient. U.S. Pat. No. 6,706,017 recognized that the use of numerous dilators in order to achieve the necessary opening for placing a tracheostomy tube is problematic. The '017 patent describes such a system as time-consuming and includes the possibility of creating tissue lesions and a false passage. Further, as described in the '017 patent, once the largest of the series of dilators is placed, the introduction of the trachea tube is often difficult because there is no protection for the tracheostomy cuff during its introduction, and this sometimes results in a rupture of the cuff. Further, such dilators are also not adapted for all the available tracheostomy tube. The solution suggested in the '017 patent is a percutaneous tracheostomy device which utilizes first and second inflatable dilators positioned about the insertion needle and insertable within the tracheostoma. The dilation device of the '017 patent is radially expandable, using a first dilator disposed about the needle and being radially expandable to provide a first degree of stoma dilation, and a second dilator disposed about the first dilator to provide a second degree of stoma dilation for the purpose of insertion of a cannula. A coiled or multiple layer sheath or tube is disposed about the dilation devices and is radially expandable in response to radial pressure from the dilation devices. After the desired diameter of expansion is achieved, the sheath is withdrawn after the cannula is placed in position. The dilator system of this '017 patent, however, is used for initial tube insertion. It does not alleviate in any way the need for frequent tube changes or the complications thereof. In addition, a one step tube insertion is not possible because the device described in the '017 patent is merely a method for inserting a commercially available, single size/type of tracheostomy tube. The device, system and method described hereinafter is not a way to simply place the well known single diameter tracheostomy tubes, but rather a new type of tracheostomy tube all together, a tube that can be made to expand and contract to various diameters depending upon desired size.

BRIEF SUMMARY OF THE INVENTION

The tracheostomy system of various embodiments of this invention includes a needle and wire guide assembly insertable percutaneously into the lumen of the trachea and a dilator including a flexible tubular body terminating at its distal end in a tapered tip portion attached to the wire guide assembly. A radially expandable or contractible outer tracheostomy tube having a tubular passageway therein is mounted about the dilator for insertion into the lumen of the trachea of the patient. Upon removal of the dilator from the radially expandable/contractible outer tracheostomy tube, a cannula of desired tubular cross-section is inserted through the tracheostomy tube. In accordance with the embodiments of this invention, a plurality of dilators of various diameters are utilized for insertion into the radially-expandable/contractible outer tracheostomy tube to radially expand the tracheostomy tube to a desired diameter to prepare the tube to receive a cannula of a certain diameter, with the outer tube automatically assuming or adjusting to a larger or smaller size depending upon the diameter of the dilator inserted whereby various sized cannulas can be inserted without having to remove the outer tracheostomy tube.

In accordance with the method of inserting the tracheostomy system, a needle and wire guide assembly is installed percutaneously through the neck and into the lumen of the trachea. A first dilator attached to the needle and wire guide assembly and having an expandable/contractible tracheostomy tube mounted about the dilator is inserted through the neck and into the lumen in order to provide a tracheal stoma of an initial diameter which is maintained by the tracheostomy tube upon removal of the first dilator and needle and wire assembly. A first cannula of a predetermined diameter is then inserted into the tracheostomy tube in order to provide a cannula air passage into the trachea lumen of an initial size. When it is necessary to change to a cannula of another diameter, a dilator and cannula assembly of a second diameter is inserted into the tracheostomy tube after the first cannula has been removed. The second dilator and cannula assembly is inserted to either expand or allow the contraction of the outer tracheostomy tube to a second diameter. The "tube" dilator is removed and the cannula is left in place to maintain the desired diameter of the tracheostomy tube.

These features of the various embodiments of this invention will now be described in more detail, but it is not intended that the description of such embodiments be considered as a limitation upon the scope of the claims.

DETAILED DESCRIPTION OF THE INVENTION

Referring to the drawings, FIGS. 1-4 illustrate the insertion of the outer, multi-layered tracheostomy tube or element of the tracheostomy system. FIGS. 5-8 illustrate insertion of a cannula of desired size within the outer tracheostomy tube such that the tracheostomy system is fully implanted and operable within the patient.

Figure 1:
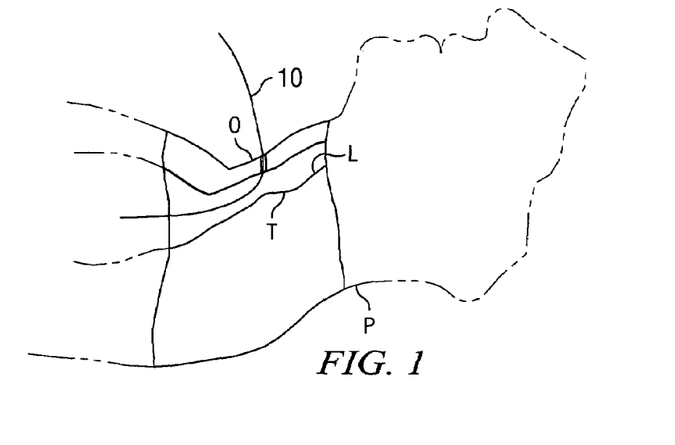
FIG. 1 is schematic view of a percutaneous opening or incision just above the trachea of a patient and showing a guide wire, which has been inserted into the lumen of the trachea.
Figure 2:
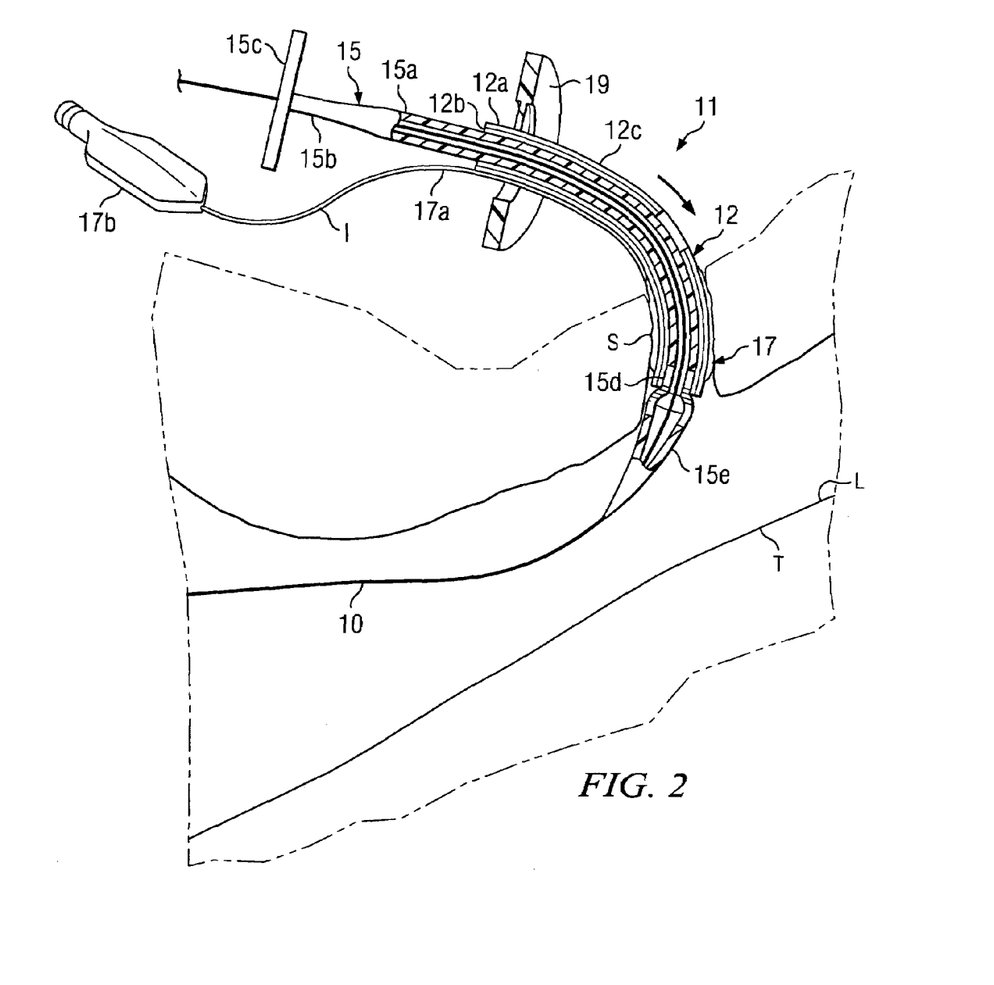
FIG. 2 is a sectional view of the tracheostomy system of this invention illustrating the insertion of a dilator having an outer radially expandable/contractible tracheostomy tube or element mounted thereover.

Referring to FIG. 1, a general schematic of a patient P is illustrated having trachea T with trachea passage way or lumen L. A guide wire 10 as is known in the art is illustrated as inserted through percutaneous opening O which has been incised in the patient, with the guide wire being fed into the trachea lumen through a needle as is known in the art. It is known to insert the guide wire through the lumen of a needle placed at the incised opening with the aid of a bronchoscope to ensure proper placement of the wire into the lumen of the trachea. After the guide wire is placed, the needle is removed. In FIGS. 1-4, the tracheostomy system generally designated as 11 is illustrated at the stage where the outer multi-layered tracheostomy tube or element 12 is partly inserted through the tracheostoma generally designated as S. The tracheostomy system 11 includes the outer tracheostomy tube 12 which is comprised of multiple layers such as layers 12a and 12b. In the embodiment illustrated, the tracheostomy tube is formed of a single sheet of resilient material such as a plastic compatible to the human body which has been formed into a coil or rolled sheath which is generally curved in FIG. 2 for insertion into the patient. The outer tracheostomy tube 12 is formed in such a manner that the tube is biased to contract toward its smallest area or diameter as illustrated in FIG. 2. However, the tracheostomy tube 12 is radially expandable by the insertion of various dilators as will be described herein so that the tracheostomy system 12 only requires the insertion of a single tracheostomy tube which can be expanded and allowed to contract as is necessary to conform to the desired diameter or area of the passageway, which houses the cannula to be described herein. It should be understood that the multi-layer outer tube may be constructed of more than one sheet of material, so long as the tube is radially expandable and biased to contract to a minimum diameter unless held in an expanded position by a cannulas larger than the minimum diameter.

Continuing to refer to FIG. 2, a dilator 15 is illustrated in cross-section. The dilator 15 is generally of a known type and includes a somewhat flexible tubular section 15a which is hollow in the center so that the dilator may be inserted onto the guide wire 10 and be guided into position in the lumen L of the trachea T of the patient. The dilator includes as its proximal end 15b a handle 15c so that the surgeon can easily insert the dilator in a known manner. Attached to the distal end 15d of the dilator is a conical tip 15e which tapers to a point but is hollow inside to receive the guide wire 10. The conical tip is designed such that the largest outer diameter is the diameter (within mm) desired to prepare the outer tube 12 to receive a cannula of certain diameter or size. As shown in FIG. 2, the dilator 15 has an outer diameter at the base 15f of the conical tip such that the outer tube 12 can be placed into the trachea stoma of the patient at a minimum initial diameter.

As illustrated in FIG. 2, the conical tip 15e of the dilator 15 is shown entering into the lumen L of the trachea. A balloon or cuff 17 is attached to the outside of the outer tracheostomy tube 12 in a manner to be described hereinafter. The balloon or expandable element 17 is connected to a tube 17a which is attached to a known inflator 17b which can be attached to a syringe in order to inflate the balloon 17 once in position within the trachea. The conical distal end potion or tip 15e of the dilator 15 is made of a plastic or other material which is sufficiently firm to enlarge or separate tissue as the dilator with the outer trachea tube 12 is inserted through the tracheostomy. A stabilizer ring or trachea tube stabilizer 19 is attached to the proximal end 12c of the trachea tube to fit against the neck of the patient and hold the outer trachea tube in its final inserted position.

Figure 3:
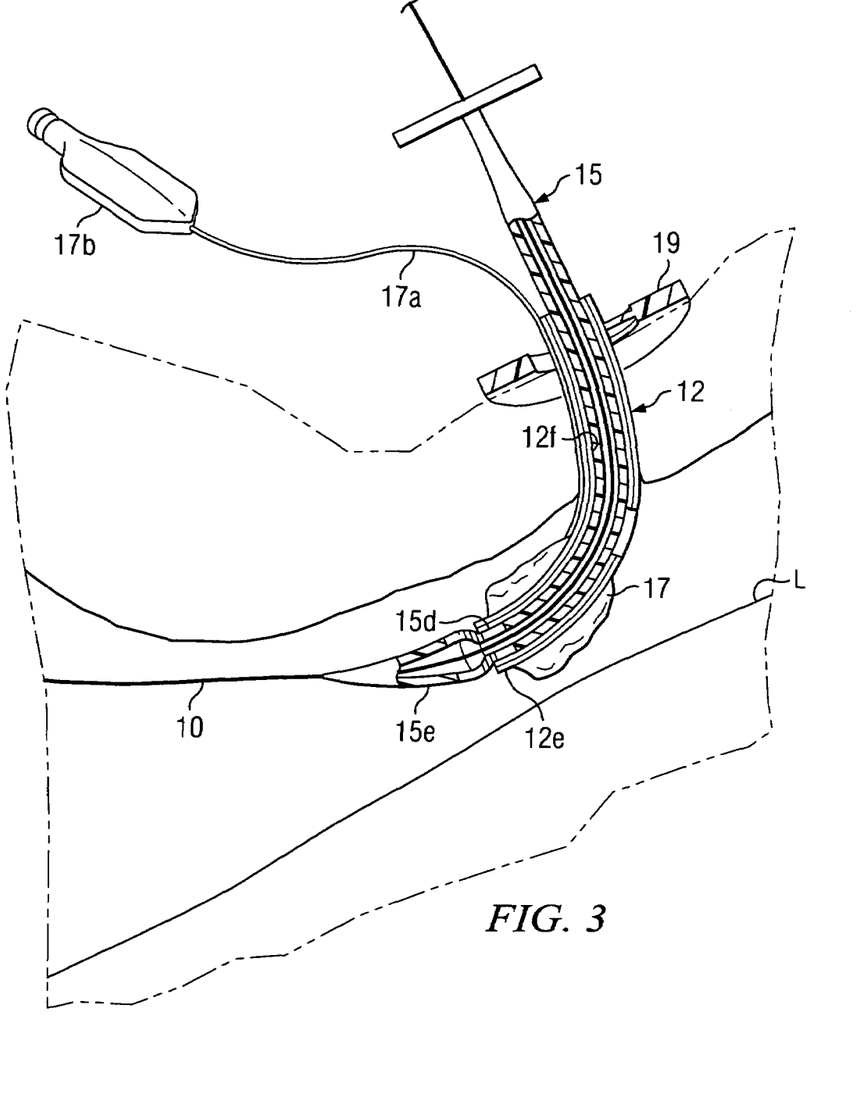
FIG. 3 is sectional view of the tracheostomy system of this invention, illustrating placement of the dilator and outer radially expandable/contractible tracheostomy tube or element of the tracheostomy system into its final position in the trachea lumen.

Referring now to FIG. 3, the dilator 15 is illustrated in a fully inserted position such that the outer trachea tube 12 has been fully inserted into a final position within the trachea stoma S and lumen L of the trachea T of the patient, with the inflatable element or balloon 17 positioned for expansion against the interior wall of the lumen.

Figure 4:
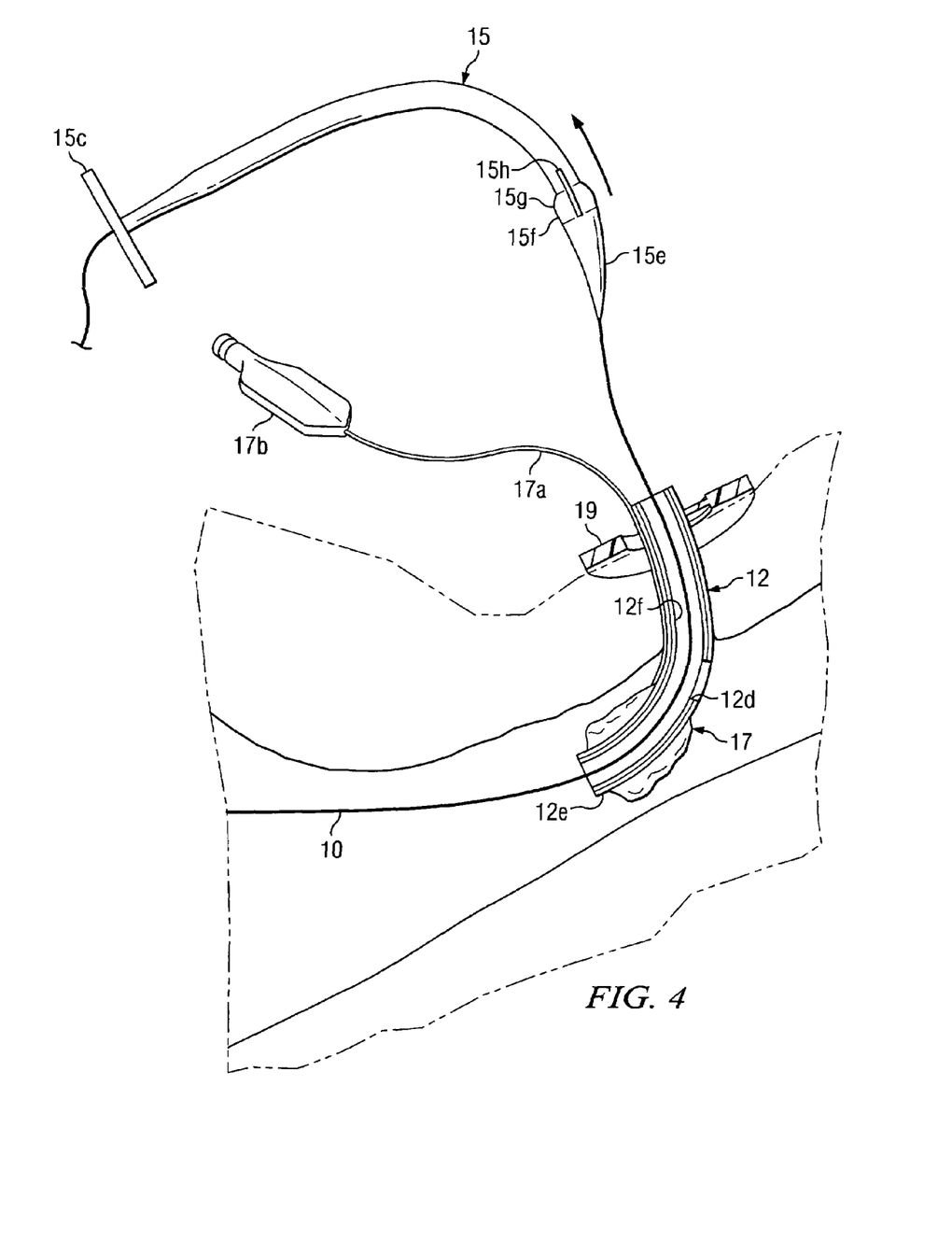
FIG. 4 illustrates the withdrawal of the dilator after the tracheostomy tube has been positioned in the trachea lumen.

Referring now to FIG. 4, the dilator 15h as been extracted, leaving in place the outer tracheostomy tube 12, which may have one or more fenestrations or openings 12d to allow the patient to breath through his or her windpipe. The stabilizer disc 19 holds the tracheostomy tube 12 in position and against movement. The conical tip 15e of the dilator is made of a firm plastic or other material, and the base of the conical tip includes a section of maximum diameter for expansion at 15f. The base 15f tapers in annular portion 15g such that after the dilator has been inserted and the forward conical or expanding section 15f pushes the tissue outwardly to form a path for insertion of the outer tracheostomy tube 12, the dilator 15 is withdrawn through the outer tracheostomy tube 12. As the dilator 15 is withdrawn as shown in FIG. 4, the tapering annular portion 15g bears against the distal end 12e of the tube and enters the passageway 12f in the outer trachea tube such that the dilator 15 can be pulled entirely through and out of the trachea tube leaving it in place as illustrated in FIG. 4. The conical tip base 15f may have one or more channels or grooves such as shown at 15h extending axially to allow the largest diameter portion 15f of the conical tip to contract. The grooves such at 15h would enhance removal of the dilator from the tracheostomy tube and cannula. The guide wire can then be pulled completely out with the dilator so that the outer trachea tube is now in place but has assumed or contracted to a minimal diameter. This minimal diameter may be assured because the dilator 15 that is utilized may be of the smallest size of the set of dilators that are used as part of the tracheostomy system. Further, because the outer tracheostomy tube is made of a single piece of an inherently resilient plastic that has been molded into a coil or sheath, the coil or sheath is biased to contract to its smallest or minimum diameter so that the passageway 12f within the outer tracheostomy tube 12 is of a minimum diameter. Whether the outer tracheostomy tube consists of a single sheet of wound or coiled plastic, or multiple pieces, the tube is designed to contract to a minimal or smaller diameter.

Figure 5:
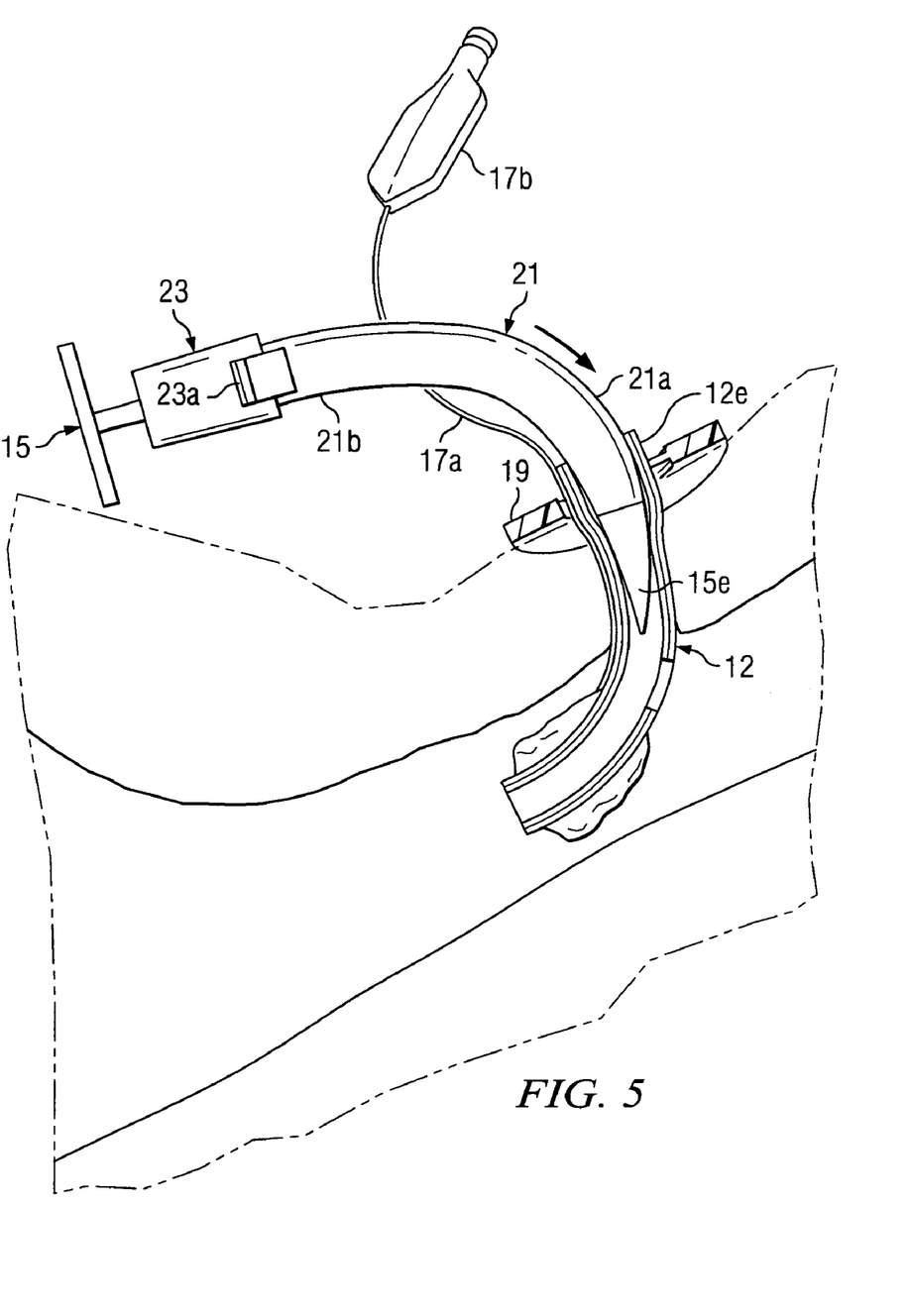
FIG. 5 illustrates the initiation of insertion of a tube dilator having a cannula located on the outside for insertion into the radially expandable/contractible tracheostomy tube.

FIGS. 5-8 illustrate the insertion of a cannula into the passageway within the outer trachea tube 12. With respect to the cannula tube of FIGS. 5-8, it should be understood that the cannula tube 21 that is initially inserted may be of a minimum diameter but that cannula tube of greater diameters or lesser diameters can be inserted into the outer trachea tube 12 as needed. That is, one cannula tube can be removed and another cannula tube inserted into the outer tube, which remains in position in the tracheostoma. Referring now to FIG. 5, cannula tube 21 is mounted onto a dilator which is located within the cannula 21 but extends through distal end 21a of the dilator such that another conical tube expanding tip 15e is shown. As the tube expanding tip 15e of the dilator 15 forces the outer tube 12 to expand, the outer tube pushes or expands the tissue of the tracheostoma outwardly. (The dilator 15 shown in FIG. 5 is identical or similar in structure to the dilator shown in FIGS. 1-3 except that now the dilator is utilized to insert the cannula 21. Cannula tubes 21 are known in the art and are formed of a relatively rigid plastic to provide a passageway into the lumen L.

Referring again to FIG. 5, the dilator 15 is illustrated as partially inserted into the outer tracheostomy multi-layered tube 12 or element, which as illustrated, is being expanded from a minimum diameter at its proximal end 12e to a greater diameter and, as the dilator tip 15e moves through the passageway of the outer tracheostomy tube 12, the entire outer tracheostomy tube 12 is expanded from a minimum diameter to a larger diameter. It should be understood, however, that the dilator 15 as illustrated in FIG. 5 may be installing a cannula of exactly the size as the diameter of the passageway of the outer tracheostomy tube as shown contracted to a minimal diameter in FIG. 5, as well as a larger diameter. Also illustrated in FIG. 5 is an adapter 23 which is generally cylindrical and is attached to opposingly mounted clips such as 23a attached to the proximal end of 21b of the cannula tube 21.

Figure 6:
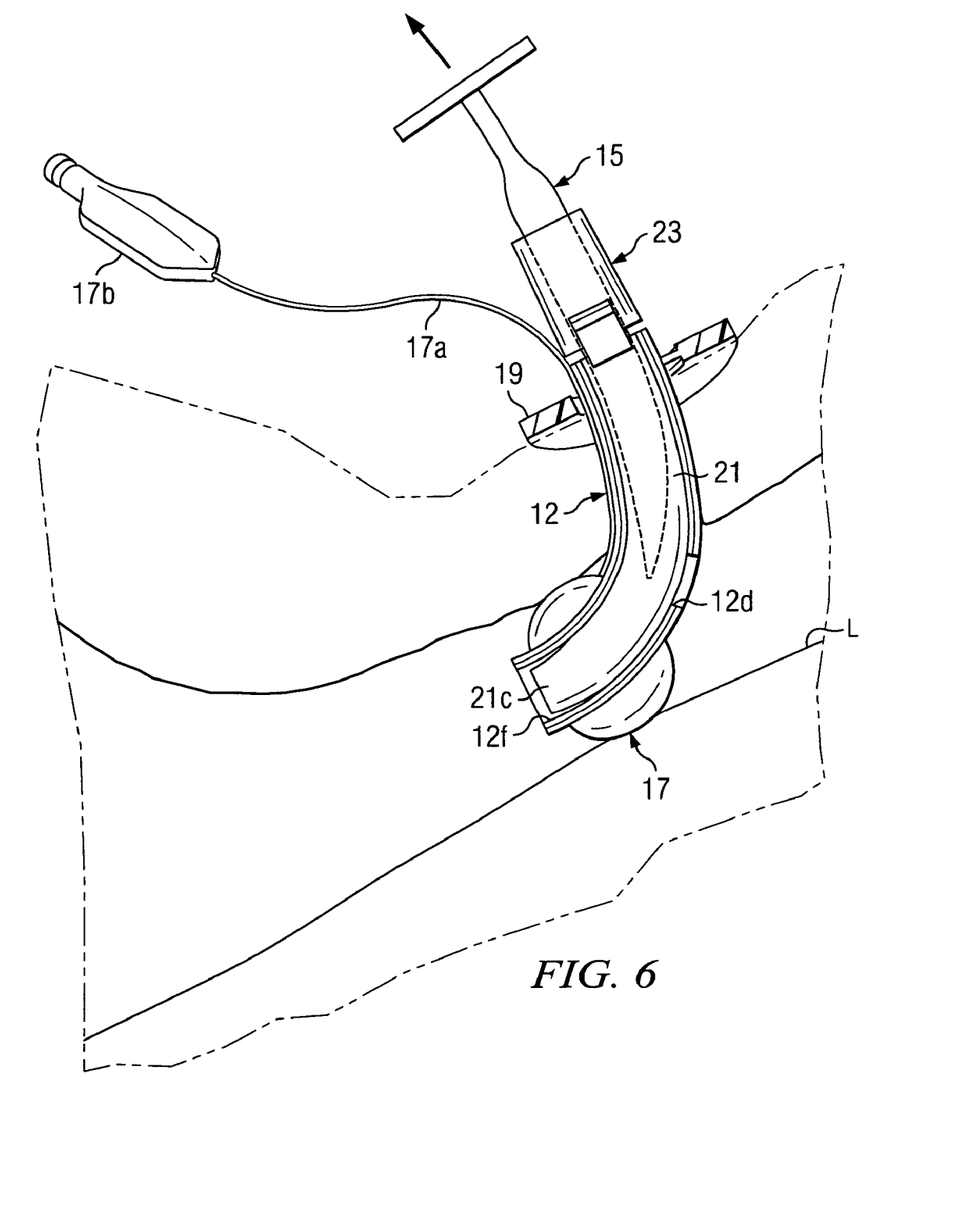
FIG. 6 illustrates the removal of the tube dilator after the cannula has been placed in position within the tracheostomy tube and the tracheostomy cuff has been expanded.

Referring now to FIG. 6, the dilator 15 has been inserted all the way through the passageway 12f of the outer tracheostomy tube such that the cannula tube 21 is fully inserted into the passageway of the outer tracheostomy tube 12 and is now in position for use. As shown in FIG. 6, the dilator 15 is actually being withdrawn through the cannula passageway 21c such that the cannula tube is now properly positioned for use, with the outer tracheostomy tube 12 having been expanded to a diameter such that the tube surrounds in juxtaposition the outer surface of the cannula tube 21. It should be understood that the cannula tube 21 as illustrated in FIG. 6 may be of various sizes. For example, initially the cannula 21 that is inserted by the procedure as shown in FIGS. 5-6 may be of a minimal size or diameter. However, if the patient either initially needs or later needs a cannula tube 21 of a larger diameter, the cannula tube, if one has already been inserted is removed and another dilator assembly as illustrated in FIG. 5, which includes a larger cannula tube 15 and dilator 21, is inserted into the outer tracheostomy tube. And, because the outer tracheostomy tube 12 has assumed a minimal diameter due to contraction after removal of the smaller cannula tube, the tracheostomy tube is re-expanded to fit the new cannula tube of larger diameter. As the outer tracheostomy tube 12 expands, there is relative movement between the layers such as 12a and 12b (FIG. 2) causing the tube 12 to expand in diameter according to the radial pressure exerted by the tip 15e of the dilator 15. As is known in the art, the cannula tube 21 is very thin but rigid plastic such that the cannula maintains the overall structure of the combination of the outer trachea tube 12 and cannula tube 21 during ventilation or other use. The standard or adaptor 23 can be attached to a ventilator or other medical device as necessary.

As shown in FIG. 6, the balloon member 17 is inflated to seal against the interior wall of the lumen L of the trachea T such that no fluids or gas can pass between the outer wall of the tracheostomy tube and the wall of the lumen L. Also as shown in FIG. 6, the outer tracheostomy tube has one or more aligned openings or fenestrations 12d.

Figure 7:
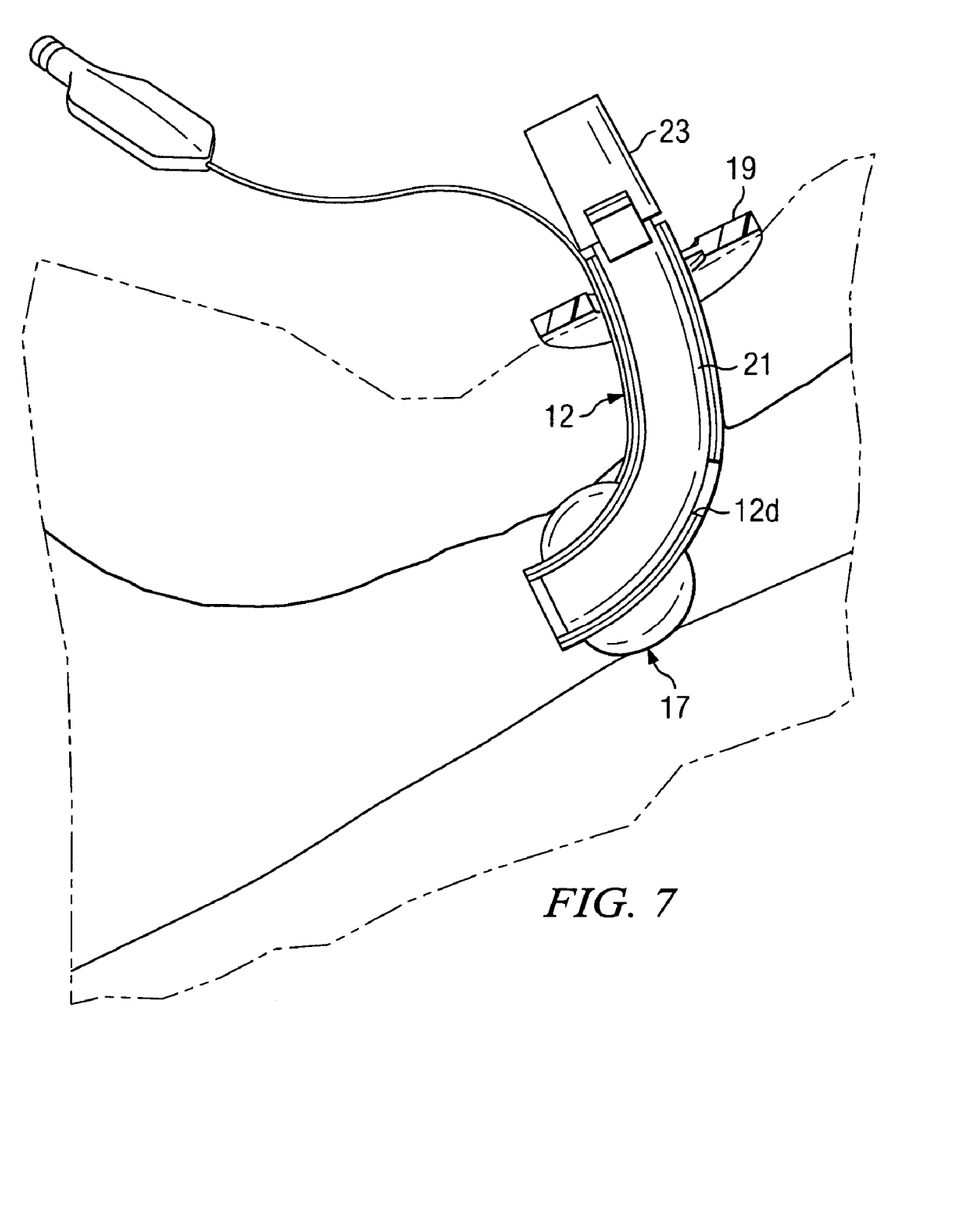
FIG. 7 illustrates the inserted cannula in final position for attachment to a ventilator or other medical equipment as necessary.

Referring now to FIG. 7, the tracheostomy system 11 is now in a fully operable or functional position, with the outer tracheostomy tube 12 expanded from the position shown in FIG. 5 to the position shown in FIG. 7. Cannula 21 is in position with the cannula standard or connector 23 ready for attachment to a ventilator or other medical device. As necessary, the cannula 21 can be withdrawn so that an even larger cannula can be inserted, with the outer tracheostomy tube being expanded to an even greater diameter. Conversely, the cannula 21 illustrated in FIG. 7 can be removed and a smaller cannula can be inserted, with the outer tracheostomy tube automatically contracting or adjusting to a smaller diameter, due to the resilient bias within the coils or layers of the tracheostomy tube to assume a position of smaller diameter.

Figure 10A:
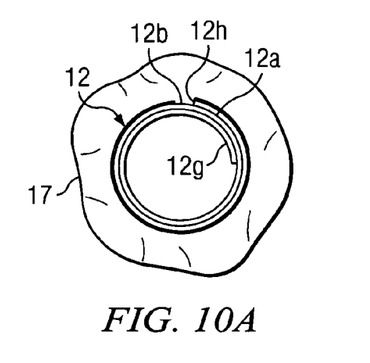
FIG. 10a illustrates the mounting of the trachea balloon about a portion of the outer layer of the outer trachea tube or sheath.
Figure 10B:
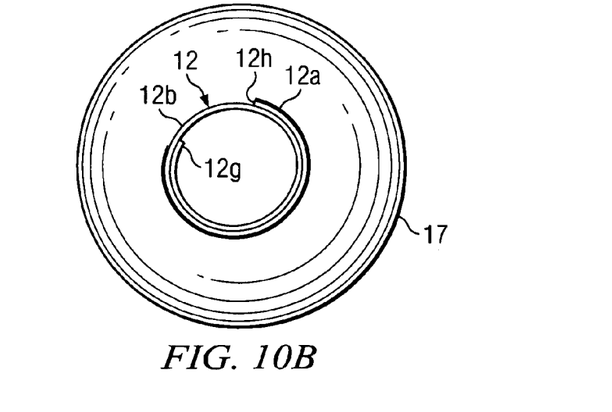
FIG. 10b illustrates the trachea balloon in an inflated position about the trachea tube.

Referring to FIG. 7 as well as FIGS. 10a and 10b, the balloon element 17 is illustrated. In FIG. 10a, the balloon or inflatable element 17 is shown in a deflated position, and the balloon 17 is shown inflated in FIG. 10b. Because the outer tracheostomy tube 12 is formed of a continuous layer of plastic or other resilient material and has several layers, the actual outer surface of the tracheostomy tube changes as the diameter of the tube changes. This also applies to the inner surface. For example, as shown in FIG. 10a, with the tracheostomy tube in a contracted position, the internal layer terminates at end 12g at a 3 o'clock position. Referring now to FIG. 10B, when the tracheostomy tube 12 is expanded, the internal end 12g moves along the intermediate layer 12b to a ten o'clock position (for illustration purposes only) thus exposing more or a greater portion of the intermediate layer of the tracheostomy tube. Similarly, the outer layer of the tracheostomy tube previously identified as 12a terminates at end 12h at approximately a one o'clock position as shown in FIG. 10A, and is shown in the same position in FIG. 10B. However, even the outer end portion 12h of external winding or layer 12a could change positions. In order for the balloon element 17 to attach to the tracheostomy tube at its outer surface and be available for expansion regardless of the diameter assumed by the tracheostomy tube, it is necessary to connect or attach the inside portion of the balloon 17 to a surface portion of the tracheostomy tube which remains exposed regardless of the diameter assumed by the multi-layer tube. This attachment is shown in FIGS. 10A and 10B so that whether the outer tracheostomy tube is in the contracted position shown in FIG. 10A or in the expanded position shown in FIG. 10B, the balloon element remains attached and is available for expansion.

Figures 8, 9A:
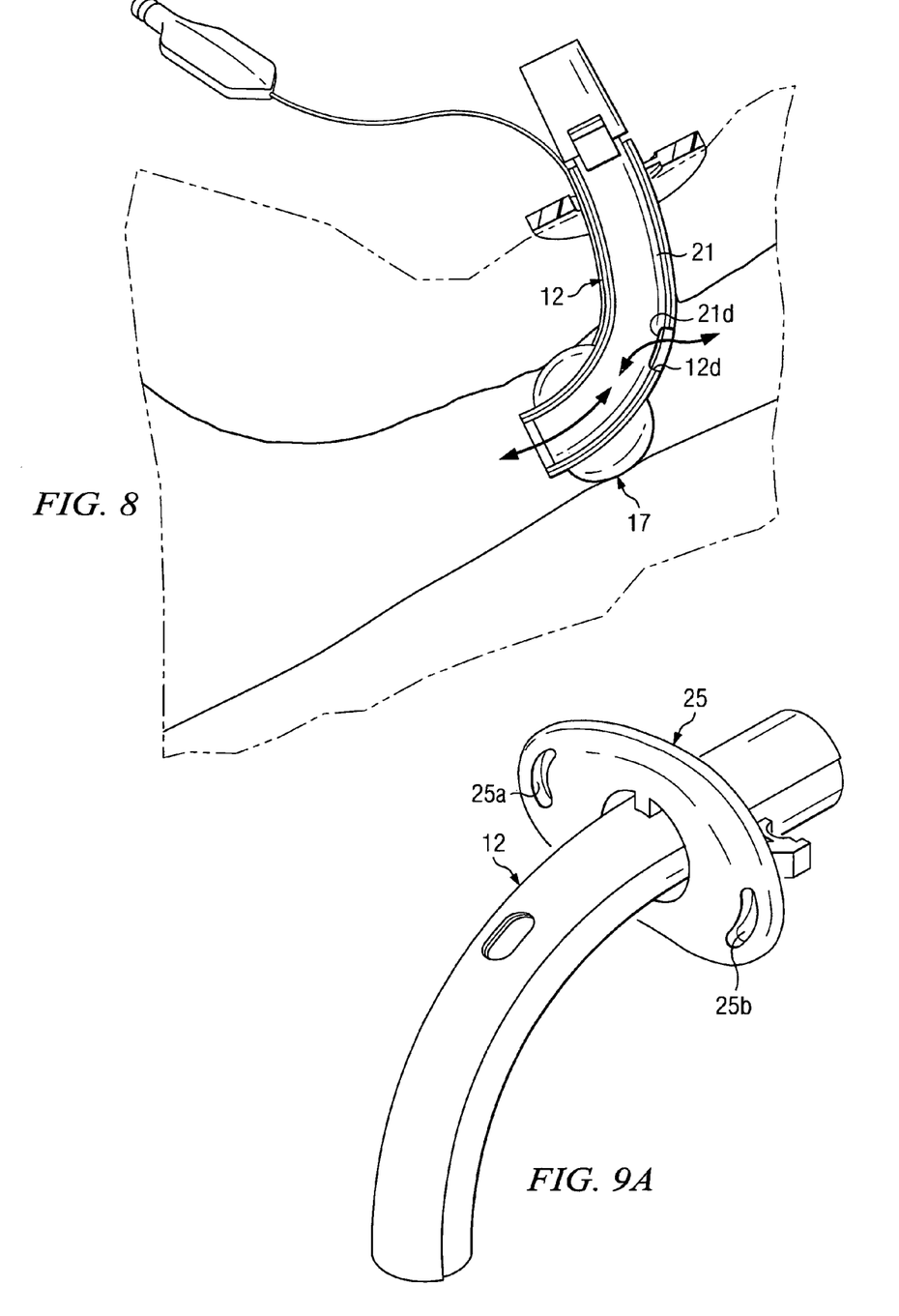
FIG. 8 is a view partially in section of the inserted outer tracheostomy tube or element and cannula illustrating an opening in the trachea tube, which is not being used as an air passage for the patient because there is no aligned opening in the cannula.
FIG. 9a is a perspective view of the trachea tube illustrating aligned fenestrations within various layers of the trachea tube.

Referring now to FIG. 8, FIG. 8 is identical to FIG. 7 except that cannula 21 includes a cannula opening or fenestration 21d which is aligned with the openings or fenestrations 12d in the outer tracheostomy tube 12. In this manner, the patient may now breathe all or part on its own since a passageway is available as shown by the arrows for communication between the lungs and the patient's windpipe.

Referring to FIG. 9a, a second version of the trachea tube stabilizer designated as 25 is illustrated mounted about the outer tracheostomy tube 12. The trachea tube stabilizer 25 includes opposing slots 25a and 25b which can receive any type of string or cord in order to secure the tracheostomy tube stabilizer onto the neck of the patient to avoid undesired movement of the system.

Figure 9B:
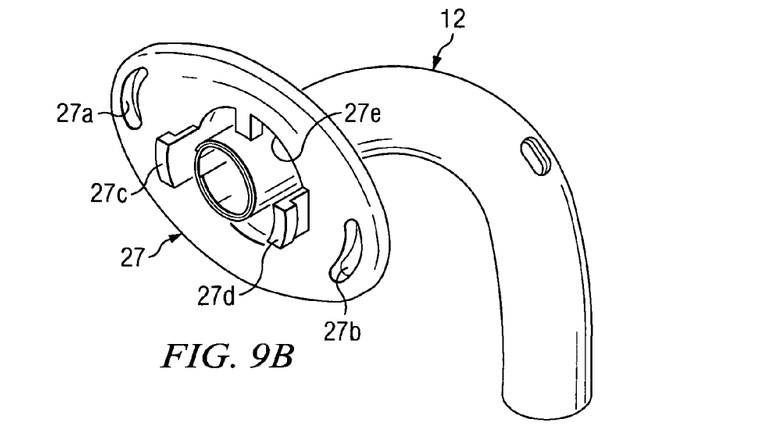
FIG. 9b illustrates the trachea tube stabilizer located at the proximal end of the trachea tube.
Figure 9C:
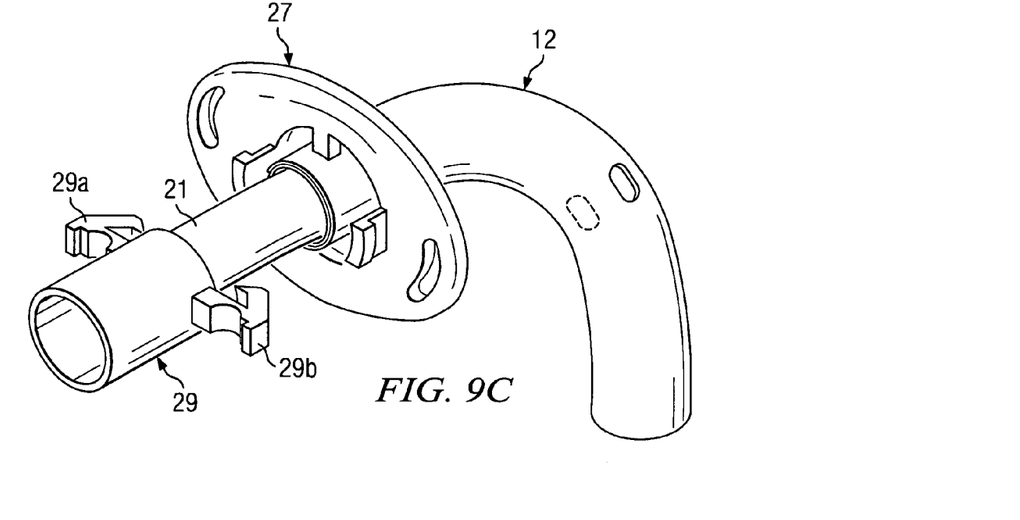
FIG. 9c illustrates the partial insertion of the cannula including a cannula standard or connector for attachment to the trachea tube stabilizer.

Referring now to FIG. 9b, a third design 27 is shown for the tracheostomy tube stabilizer. In this design, slots 27a and 27b on opposite sides of the generally elliptically shaped stabilizer disk provide for tying the stabilizer about the neck of the patient. Further, the size of the internal opening 27e in the stabilizer, which is generally elliptically shaped, is sufficiently large to accommodate various sizes of the tracheostomy tube 12 as it moves between expanded and contracted positions. The stabilizer 27 further includes connector elements 27c and 27d which are formed with the stabilizer and extend outwardly to receive a cannula standard 29 which is attached to the proximal end of the cannula 21. The cannula standard includes connector elements 29a and 29b for rotation into a locked position over the mating connector elements 27c and 27d, respectively, of the stabilizer 27. In this manner, not only is the stabilizer 27 held in position such that the tracheostomy tube is secured, but also the cannula 21 is locked into position against the stabilizer so that the cannula is also fully secure. FIG. 9c illustrates an opening 12 in the outside layer with another opening shown in dotted lines in an internal layer. Only when the tube 12 is expanded or contracted to a certain size do these openings align in order to align with the opening in the cannula to allow the air to flow through the walls of the tube.

The trachea system 11 of this invention has been described with respect to its installation as shown in FIGS. 1-4 for insertion of the outer trachea tube itself, and for insertion of cannulas 21 of various diameters as shown in FIGS. 5-7. It should be understood that while the cannula 12 has been described as a known cannula structure and shape, cannulas of other configurations may be used. Further, while the outer trachea tube has been described as being formed of a single sheet of wound or coiled plastic, other structures for a radial expandable and contractible trachea tube are also envisioned, as well as materials besides plastic, so long as the material is fully compatible with the human body. While the description of the tracheostomy system 11 has been described with respect to the utilization of a tracheostomy tube, which is capable of assuming various diameters, it is also within the scope of this invention to utilize more than one tracheostomy tube should it be necessary to provide for additional expansion of the tracheostoma or to provide aligned openings as needed for formation of a fenestration, or to assume different minimum diameters.

The description of the embodiments illustrated is exemplary, and other configurations may be utilized within the scope of the inventions. For example, the outer tracheostomy tubes may be provided with or without fenestrations. The cannula tubes and outer tracheostomy tubes may be provided in multiple diameters and lengths, and cuffs may or may not be attached to the tracheostomy tubes.

I claim:

1. A tracheostomy system, comprising:
    a needle and wire guide assembly adapted for percutaneous insertion through an incision into a lumen of a trachea of a patient;
    a dilator comprising a flexible tubular body terminating at its distal end in a tapered portion attached to said wire guide assembly;
    a radially variable diameter tracheostomy tube having a coiled tubular passageway to receive said dilator for radial expansion of radially variable diameter tracheostomy tube;
    a plurality of fenestrations, formed in a surface of the radially variable diameter tracheostomy tube and aligned with each other at a predetermined diameter of the radially variable diameter tracheostomy tube, forming a passageway through the surface of the radially variable diameter tracheostomy tube;
    a cannula having a tubular cross-section, and distal and proximal ends, to provide an airway, said cannula being substantially rigid and curved for insertion into said radially variable diameter tracheostomy tube and being insertable at its distal end into the lumen of the trachea and having a proximal end exposed at the proximal end of the tracheostomy tube for attachment to a ventilator or other medical devices,
    wherein the variable diameter tracheostomy tube remains positioned in the trachea after insertion to receive various sizes of cannula tubes without removal of the variable diameter tracheostomy tube.

2. The structure set forth in claim 1, including:
    a plurality of dilator assemblies of various diameters for insertion into said radially variable diameter tracheostomy tube to radially expand said tracheostomy tube to various diameters; and
    each of said dilator assemblies having a cannula of a different diameter for insertion into said tracheostomy tube in order to provide internal airways of various sizes.

3. The structure set forth in claim 1, wherein:
said radially variable diameter tracheostomy tube is formed of a continuous section of material which is wound into a coil or tube to form said tubular passageway, said tube being radially expandable or contractible by insertion of said dilator assemblies of various diameters.

4. The structure set forth in claim 3, wherein:
said radially variable diameter tracheostomy tube is formed of a resilient material which, upon forming into a coil or sheath, has an intrinsic bias to contract to a smaller diameter to reduce the size of said tubular passageway.

5. The structure set forth in claim 4, including:
said radially variable diameter tracheostomy tube being formed of a sheet of resilient plastic wound into layers movable with respect to each other such that said tracheostomy tube is biased to contract toward a minimum diameter.

6. The structure set forth in claim 1, further comprising:
a fenestration formed in a surface of the cannula near the distal end, adapted for positioning within said trachea lumen upon insertion into the patient, the fenestration of the cannula adapted to align with the plurality of fenestrations of the radially variable diameter tracheostomy tube, forming a airway through the radially variable diameter tracheostomy tube and the cannula that bypasses
the proximal end of the tracheostomy tube,
whereby air can pass through the airway and through the vocal chords of the patient allowing for phonation and breathing.

7. A tracheostomy device, comprising:
a radially variable diameter coiled tracheostomy tube adapted for insertion through a tracheostoma between an incision in the neck and the trachea lumen of a patient, said tracheostomy tube forming a tubular passage way; and
a plurality of fenestrations, formed in a surface of the radially variable diameter tracheostomy tube and aligned with each other at a predetermined diameter of the radially variable diameter tracheostomy tube, forming a passageway through the surface of the variable diameter tracheostomy tube;
a cannula positioned within said tracheostomy tube and terminating at its distal end within the trachea lumen, and having a proximal end adapted to connect to a ventilator or other medical equipment,
wherein the variable diameter tracheostomy tube is adapted to remain positioned in the tracheostoma to receive various sizes of cannula tubes without removal of the variable diameter tracheostomy tube.

8. The structure set forth in claim 7, further including:
an expandable balloon cuff attached to said tracheostomy tube near its distal end and adapted for positioning within the patient's lumen;
a flow tube extending from attachment to said balloon outwardly through said tracheostoma into connection with an inflate means for inflating and deflating said balloon cuff as desired.

9. The structure set forth in claim 7, further comprising:
a fenestration formed in a surface of the cannula adapted to align with the plurality of fenestrations of tracheostomy tube.

10. The structure set forth in claim 7, further including:
a stabilizer ring attached to the proximal end of said tracheostomy tube adapted for placement against the neck of the patient and having means to stabilize the position of said ring and said tracheostomy tube with respect to said tracheostoma.

11. A tracheostomy tube, comprising:
a radially variable diameter tube formed a longitudinally coiled sheet of resilient material and adapted to be inserted into a tracheostoma, and further adapted to receive various sizes of cannula tubes without removal of the radially variable diameter tube from the tracheostoma; and
a plurality of fenestrations, formed in a surface of the radially variable diameter tube and aligned with each other at a predetermined diameter of the radially variable diameter tube, forming a passageway through the surface of the radially variable diameter tube.

12. A tracheostomy system, comprising:
a radially variable diameter tracheostomy tube having a coiled tubular passageway, having a minimum diameter and a maximum diameter; a plurality of fenestrations, formed in a surface of the radially variable diameter tracheostomy tube and aligned with each other at a predetermined diameter of the radially variable diameter tracheostomy tube, forming a passageway through the surface of the variable diameter tracheostomy tube;
a cannula of a substantially rigid material of a predetermined diameter between the minimum diameter and maximum diameter of the radially variable diameter tracheostomy tube, adapted for insertion into the radially variable diameter tracheostomy tube, thereby expanding the radially variable diameter tracheostomy tube,
wherein the radially variable diameter tracheostomy tube is biased to contract to the minimum diameter unless held in an expanded position by the cannula.

13. The tracheostomy tube of claim 12, further comprising:
a dilator comprising a flexible tubular body terminating at one end in a tapered portion, adapted for insertion through the cannula, the tapered portion exposed beyond and end of the cannula and configured to expand the radially variable diameter tracheostomy tube from the minimum diameter to the diameter of the cannula,
wherein insertion of the dilator and cannula expands the radially variable tracheostomy tube to the predetermined diameter of the cannula.

14. The tracheostomy tube of claim 12, further comprising:
a fenestration formed in a surface of the cannula, adapted to align with the plurality of fenestrations of the radially variable diameter tracheostomy tube, forming a airway through the surface of the radially variable diameter tracheostomy tube and the surface of the cannula.

* * * * *